(12) United States Patent
Johnson

(10) Patent No.: US 8,449,484 B2
(45) Date of Patent: May 28, 2013

(54) CONFORMABLE BACK BRACE

(76) Inventor: Willie Neil Johnson, Bradenton, FL (US)

( * ) Notice: Subject to any disclaimer, the term of this patent is extended or adjusted under 35 U.S.C. 154(b) by 104 days.

(21) Appl. No.: 13/060,434

(22) PCT Filed: Aug. 20, 2009

(86) PCT No.: PCT/US2009/054450
§ 371 (c)(1), (2), (4) Date: Feb. 23, 2011

(87) PCT Pub. No.: WO2010/027689
PCT Pub. Date: Mar. 11, 2010

(65) Prior Publication Data
US 2011/0144551 A1 Jun. 16, 2011

Related U.S. Application Data

(60) Provisional application No. 61/091,426, filed on Aug. 24, 2008.

(51) Int. Cl.
*A61F 5/00* (2006.01)
(52) U.S. Cl.
USPC .............................................. 602/18; 128/876
(58) Field of Classification Search
USPC ........... 602/19; 128/96.1, 876; 2/44, 336–338
See application file for complete search history.

(56) References Cited

U.S. PATENT DOCUMENTS 5,232,424 A * 8/1993 Pearson et al. ................ 482/106
6,099,490 A * 8/2000 Turtzo ............................. 602/19

FOREIGN PATENT DOCUMENTS

JP 2001-314210 * 11/2001

* cited by examiner

*Primary Examiner* — Michael A. Brown
(74) *Attorney, Agent, or Firm* — Dorothy S. Morse

(57) ABSTRACT

A conformable brace used for supporting both the abdomen and lower back of a wearer in preventative and treatment applications. The brace includes an abdominal support panel (110) substantially enclosed within a support envelope (120), a lumbar support panel (210) having a dome-shaped protrusion (240) that complements the lumbar contour of the user's back, and a belt (320) that places the abdominal support panel (110) and the lumbar support panel (210) in opposed biasing arrangement against the torso of a user. The belt (320) is associated with the support envelope (120) and is also inserted though vertical slots (220) in the lumbar support panel (210). The belt (320) is used for infinitely adjustably selection of the biasing force needed by each user, the support envelope (120) evenly distributes the tension provided by the belt (320) across the abdominal support panel (110) for enhanced user comfort, and a Y-shaped end tab (400) comprising easily-releasable material helps the belt to remain secure during its use.

21 Claims, 14 Drawing Sheets

CONFORMABLE BACK BRACE

TECHNICAL FIELD

Presented herein is a multi-component brace assembly primarily intended for providing immobilization of the human back, and more particularly to a conformable back brace employed for providing simultaneous abdominal and lumbar support to the user so as to realign and tone muscles in the area of the user's back and stomach. Both preventative and treatment applications are contemplated. In addition, it has a lightweight construction, can easily and promptly be custom-fit to a user, is quickly and easily placed into its usable position around the torso by its user once custom-fit, and it has a slim profile that allows easy concealment under clothing according to user preference and/or need.

BACKGROUND ART

Spinal and lower back muscle pain are chronic problems for many people. This type of pain, particularly evident in older or overweight individuals, can easily be aggravated by many types of body trauma, such as but not limited to heavy lifting and strenuous physical activity. Furthermore, the prescription drugs used to alleviate lower back pain, and are not always effective. In addition, even day-to-day activity requiring movement of the back can lead to further muscular aggravation, only to reach the point in some individuals where all but the most potent pain relief medication is needed to have any effect.

In order to help alleviate lower back pain, prevent future injury, and/or aid in recovery, a wide variety of muscular strain reducing devices for the lower back have been tried, ranging from elastic wrap-type supports to individual solid support fixtures placed longitudinally along the back to restrain its movement. However, many of these longitudinally-extending devices have the disadvantages of being very heavy, too hot to wear, burdensome by unduly restricting movement, and/or do not provide the proper support and alignment to be useful.

It is apparent from the prior art devices currently available, that a device is needed, and is not previously known, which is able to provide simultaneous lumbar and abdominal support and alignment, while being lightweight, comfortable, readily custom-fit, and easily and quickly adjustable by its user according to need. The device should also lend itself to being worn not only while sedentary, but also during strenuous physical activity, such as but not limited to golf, tennis or other sports, in the work place while one sits for long periods, and when any physical work is required.

DISCLOSURE OF INVENTION

In one aspect, presented is a multi-component conformable back brace that comprises an abdominal support panel and an opposingly positioned lumbar support panel, which also has an improved and easy-to-secure strapping system that positions and biases both panels around the torso of a user. In one aspect, the belt of the strapping system is made from material that can be securely mated to the hook portion of a hook-and-loop fastener. Furthermore, an end tab secured to one end of the belt has an advantageous structure that facilitates secure attachment and easy release of each opposing end of the present invention belt, while also preventing inadvertent engagement of any part of the strapping system with clothing positioned over it. In one exemplary aspect, cushioning is associated with each panel to enhance its comfort during use.

In addition, one support member, can be totally or substantially enveloped within a pouch associated with the strapping system that evenly distributes forces across the panel inside it for increased user comfort. The panel not situated in the envelope/pouch will have vertically-oriented slots on its opposing ends through which the distal ends of the strapping system belt can be inserted to connect it and the opposing panel in the envelope/pouch around the torso of a user. Although the abdominal and lumbar support panels are each generally conformable to the peripheral torso shape of a human being in front and back body areas for simultaneous support thereof, the lumbar support panel extends longitudinally across the surface of a user's lower back and includes a centrally located convex dome configured to protrude into the lower central lumbar portion of its user's back. The positioning of this dome provides an ideal back profile that allows the present invention to realign and tone back and stomach muscles in both preventative and treatment applications. The lower central lumbar region of the lower back is often the most troublesome area for treating/reducing back pain, since its shape makes it difficult to support.

In one aspect, the abdominal support panel would already be inserted into its envelope/pouch during manufacture and there would be no easily-opened fastener (such as VELCRO or a zipper) to allow removal of the inserted panel from the envelope/pouch by the user. Although one or more fasteners could be present in the envelope/pouch to allow removal of the abdominal support panel as needed (such as to facilitate laundering of the strapping system), lack of fasteners will ensure that the abdominal support panel remains in its needed upright position of use. However, when the envelope/pouch is configured to fit closely around the abdominal support panel, incorrect orientation of the abdominal support panel by the user is avoided. Inversion of the lumbar support panel is not an issue, as its shape allows it to work equally well in an upright or upside down orientation. As a result, a user of the present invention is generally presented with two sub-assemblies to manipulate for custom-fitting and use, the lumbar support panel and the strapping system with its associated envelope/pouch already holding the abdominal support panel. Prior to moving the abdominal support panel, lumbar support panel, and strapping system close to a user's torso, the user would place one of the distal ends of the strapping system's belt through a vertical slot on one end of the lumbar support panel. Subsequently, and with all of the components of the present invention conformable back brace close to the torso, the user would then insert the other distal end of the belt through a vertical slot on the other end of the lumbar support panel. After positioning the envelope/pouch over the abdomen and the lumbar support panel across the lower back, all that remains for the user to do is to grasp each distal end of the belt in the present invention strapping system with a different hand and pull both distal ends forwardly toward the envelope/pouch. Once initial length adjustment of each of the opposing ends of the belt has occurred by trimming excess belt material therefrom and attaching a specifically configured end tab to one of the belt's distal ends so that the end tab and the opposing distal end of the belt each extend over a substantial portion of the strip of hook material extending horizontally in front of the envelope/pouch (this custom-fitting process is assisted by coins of hook material positioned on the belt near to the envelope/pouch), securing the two support panels into their optimal positions of use is easily accomplished by a simple and quick fastening of the ends of the present invention belt to the strip of hook material extending in front of the envelope/pouch. Tension derived from the belt is spread across the envelope/pouch, evenly dispersing force on the abdominal support panel (or in reverse across the lumbar support panel should it be placed in the envelope/pouch instead). In prior art devices, force is applied to the ends of the abdominal support panel via slots, which in addition to causing user discomfort, also placed such abdominal support panels at risk for cracking and breaking. The end tab can be used to securely fasten the distal ends of the present invention strapping system belt generally has a Y-shape with selected surfaces having hook material, and other surfaces without hooked material, so as to prevent inadvertent engagement with any user clothing positioned over it. Release of the present invention from around the torso of its user is also fast and easy, with both distal ends of the belt being easily released from the front strip of hook material extending in front of the envelope/pouch. The user can then withdraw one of the distal ends of the belt from the lumbar support panel to provide an opening to use for present invention removal from the torso. Movements made by the user in attaching and releasing the present invention from around his or her torso, including the pulling forward of both distal ends of the belt toward the envelope/pouch, are movements that one with back pain can easily accomplish with minimal discomfort.

BRIEF DESCRIPTION OF THE DRAWINGS

These and other features of the preferred embodiments of the invention will become more apparent in the detailed description in which reference is made to the appended drawings wherein.

COMPONENT LIST

Figure 1:
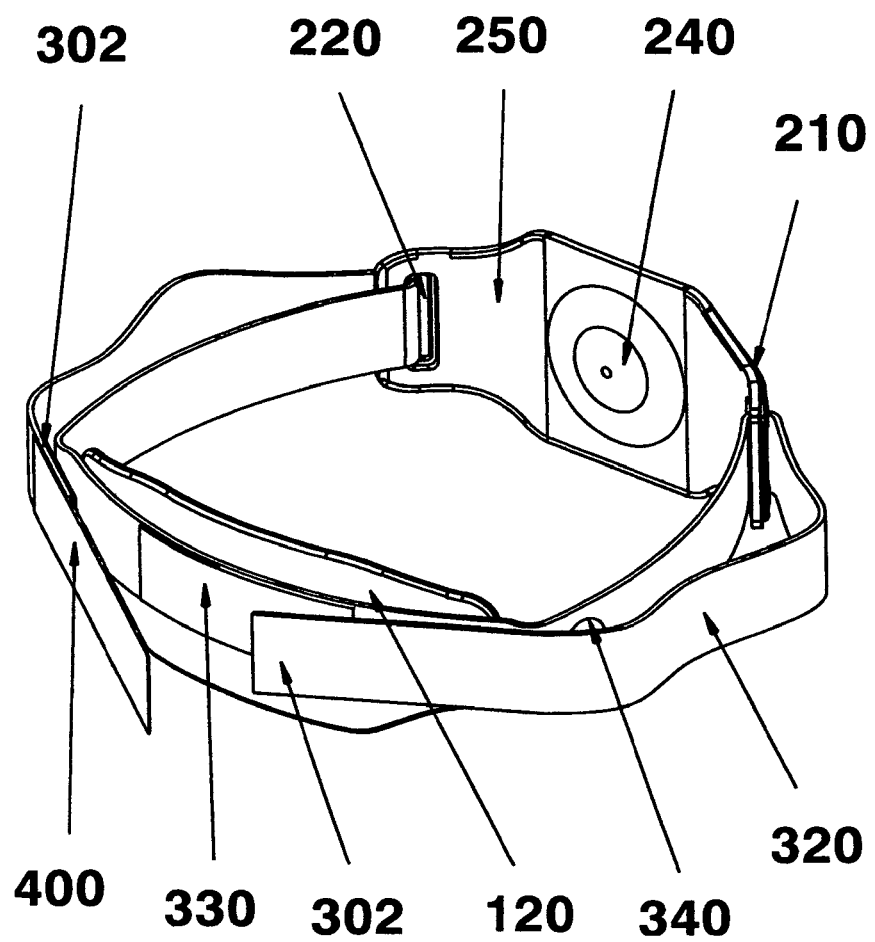
FIG. 1 is a perspective view of one aspect of a conformable back brace.

100—Combined Assembly of the back belt
110—Rigid Abdominal Support Panel
112—Hole in Abdominal Support Panel
120—Envelope/Pouch
122—Pouch Front Member
124—Pouch Back Member
200—Lumbar Support Assembly
210—Rigid Lumbar Support Panel
212—Hole in Lumbar Support Panel
220—Vertical Slot
230—Slot Reinforcement
240—Dome
250—Foam Backing
260—Adhesive
270—Stitching
300—Strapping System
302—Distal End of Belt 320
310—Belt Assembly
320—Belt
330—Strip of Hook Material
340—Circular-shaped Coin of Hook Material
400—End Tab Assembly
410—Elongated Member of End Tab Assembly 400
420—Short Member of End Tab Assembly 400
422—Interior Face of each Leg 440
424—Exterior Face of each Leg 440
430—Heat Weld
440—Two Leg Portions

BEST MODES FOR CARRYING OUT THE INVENTION

The present invention devices, systems, and/or methods can be understood more readily by reference to the following detailed description, examples, drawing, and claims, and all previous and following descriptions herein. However, it is to be understood that the present invention is not limited to the specific devices, systems, and/or methods disclosed unless otherwise specified, and as such of course can vary. It is also to be understood that the terminology used herein is for the purpose of describing particular aspects only and is not intended to be construed as limiting. The following description of the invention is provided as an enabling teaching of the invention in its best, currently known embodiment. To this end, those skilled in the relevant art will recognize and appreciate that many changes can be made to the various aspects of the invention described herein, while still obtaining the beneficial results of the present invention. It will also be apparent that some of the desired benefits of the present invention can be obtained by selecting some of the features of the present invention without utilizing other disclosed features. Accordingly, those who work in the art will recognize that many modifications and adaptations to the present invention are possible, and can even be desirable in certain applications, and should be considered as a part of the present invention. Thus, the following description should be construed as illustrative of the principles of the present invention, and not providing limitations thereto.

As used throughout, the singular forms "a," "an" and "the" include plural referents unless the context clearly dictates otherwise. Thus, for example, reference to "a belt" can include two or more such belts unless the context specifically indicates otherwise. Also, ranges can be expressed herein in at least one aspect of the present invention as from "about" one particular value and/or to "about" another particular value. In addition, when a range is expressed, it can also include from "one particular value" and/or to "another particular value". Similarly, when values are expressed as approximations, by use of the antecedent "approximately" or "about," it will be understood that the particular value also forms another aspect to be used for interpretation of the range. It is to be further understood that the endpoints of each of the ranges are significant both in relation to the other endpoint, and independently of the other endpoint. Furthermore, as used herein, the terms "optional" or "optionally" mean that the subsequently described event or circumstance may or may not occur, and that the description includes instances where said event or circumstance occurs and instances where it does not.

With reference to the accompanying FIGS. 1-14, the multi-component conformable back brace comprises an abdominal support panel 110 and a lumbar support assembly 200 that are joined together via a strapping system 300 for biasing in opposed positions to one another around the torso of a user (not shown). Although both the abdominal support panel 110 and lumbar support assembly 200 are generally configured to conform to adjacent portions of a wearer's peripheral torso, the lumbar support assembly 200 includes a lumbar support panel 210 with a centrally-located dome 240 that protrudes inwardly toward the lower lumbar region of the wearer's back, thereby providing a contour ideally complementary to the proper profile of a human back, as the lumbar support panel 210 that supportively extends longitudinally across the wearer's lower back and in combination with the abdominal support panel 110 realigns and tones muscles in the user's back and stomach areas.

Figure 2:
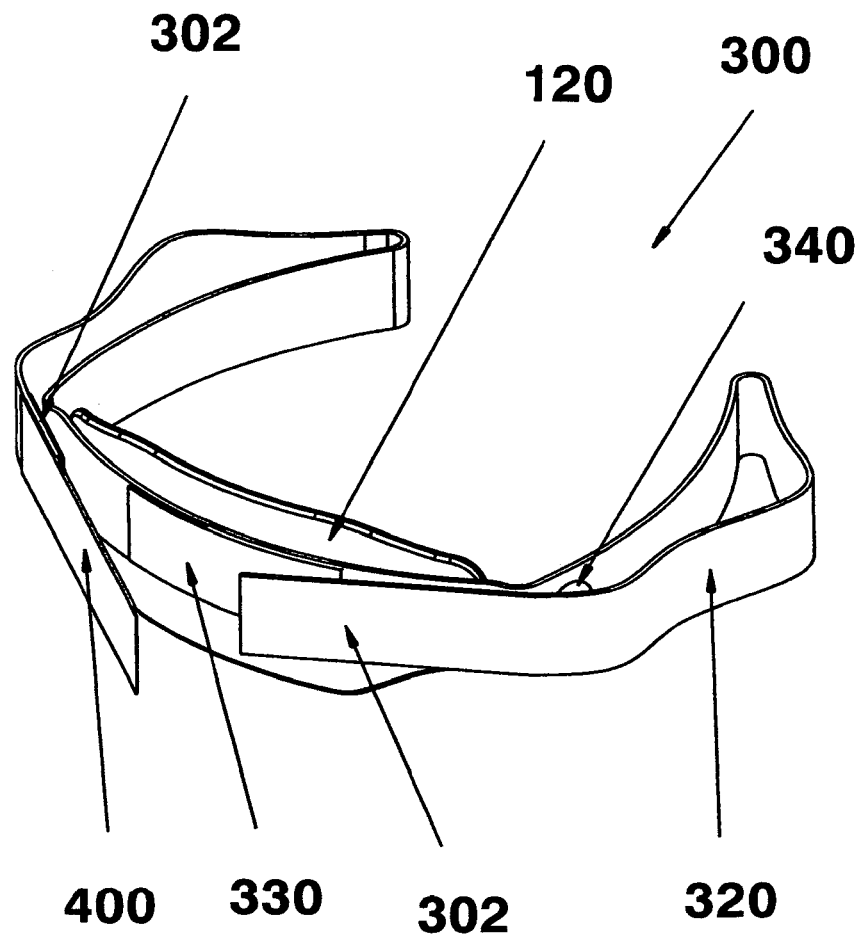
FIG. 2 is a perspective view of the strapping system of the back brace of FIG. 1.
Figure 3:
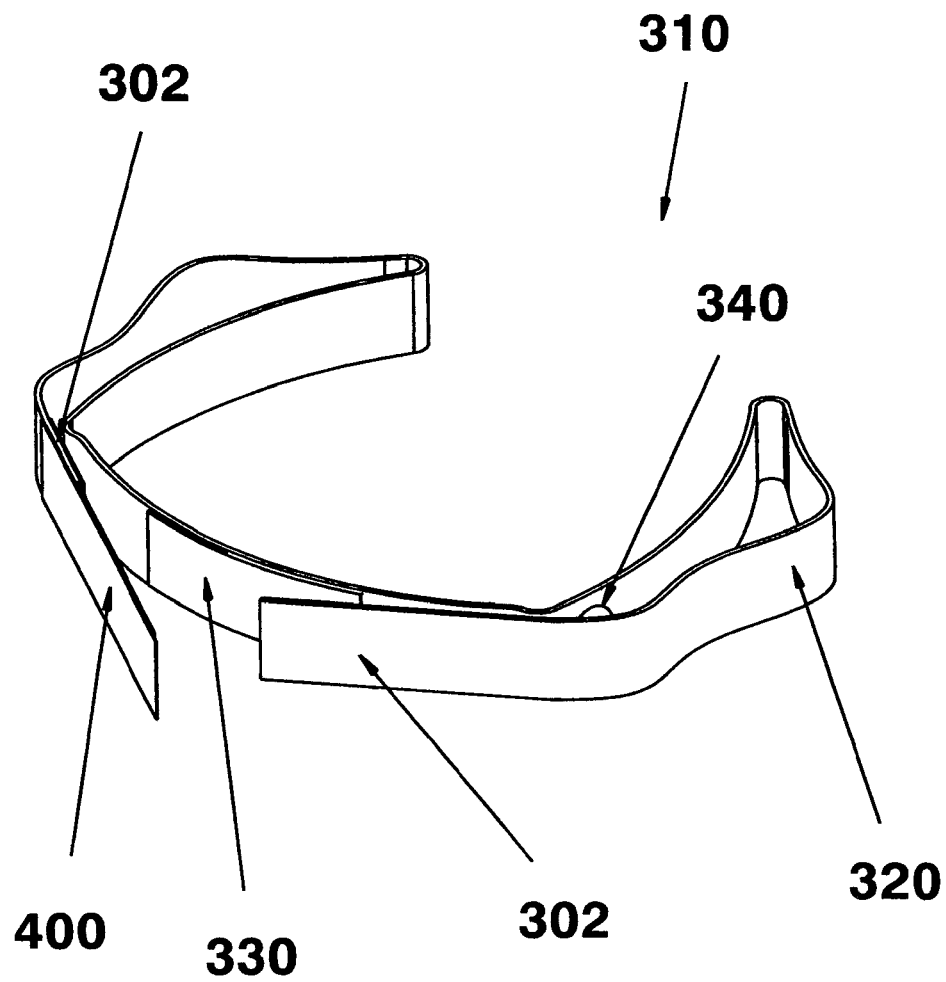
FIG. 3 is a perspective view of a belt assembly used as a part of the strapping system with the back brace of FIG. 1.
Figure 4:
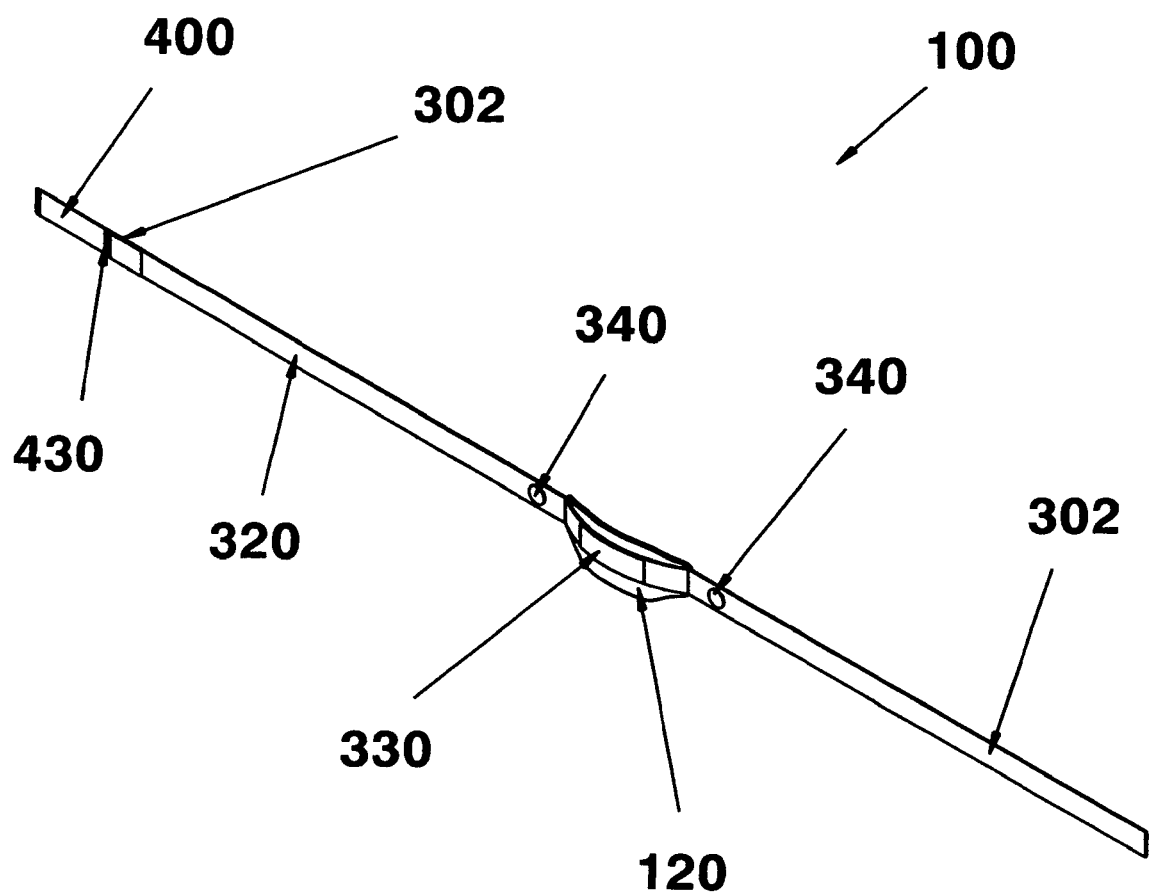
FIG. 4 is a perspective view of the strapping system of FIG. 3, illustrating a pouch for enclosing a rigid support panel.
Figure 5:
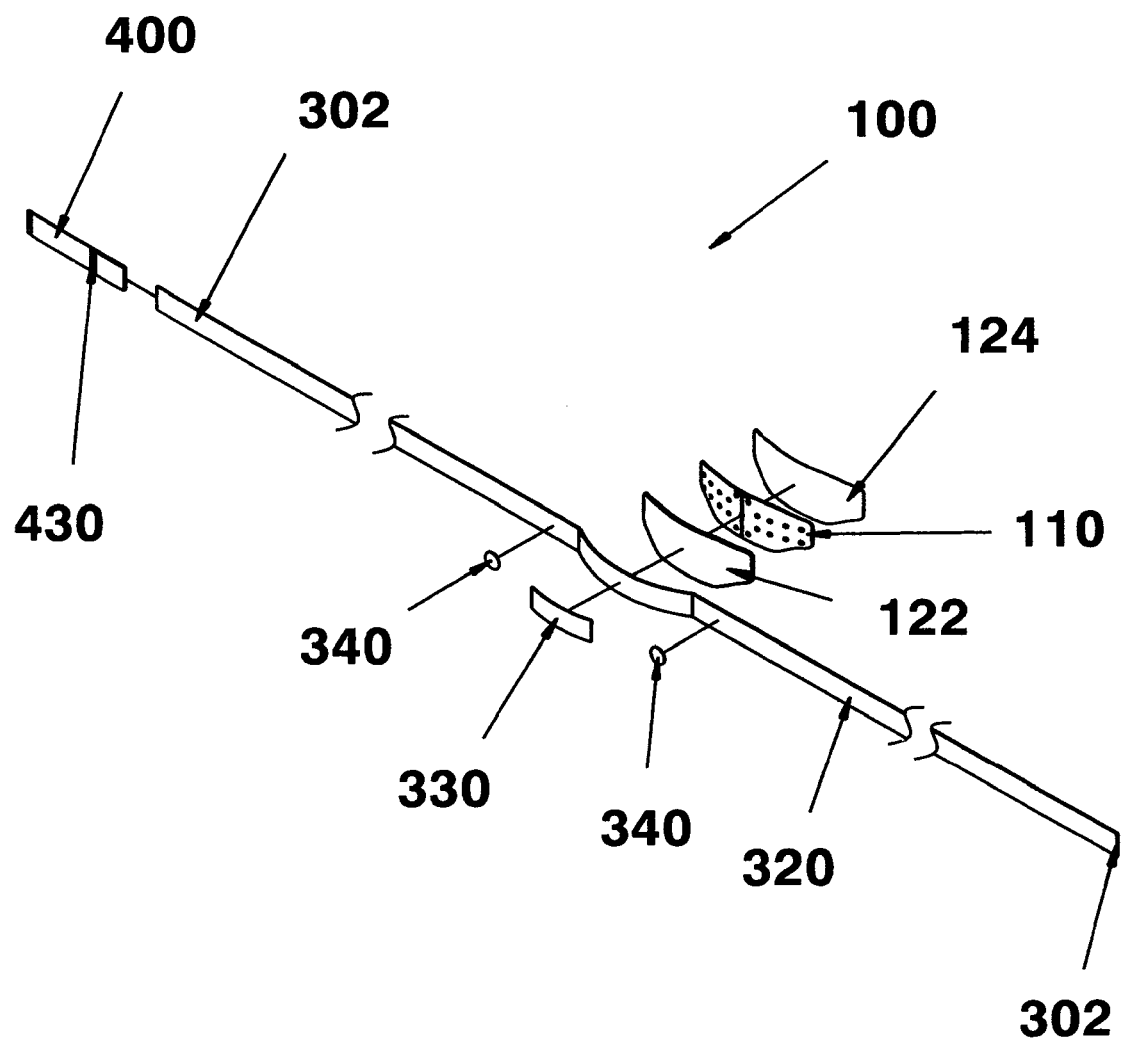
FIG. 5 is an exploded view of the strapping system of FIG. 4.
Figure 6:
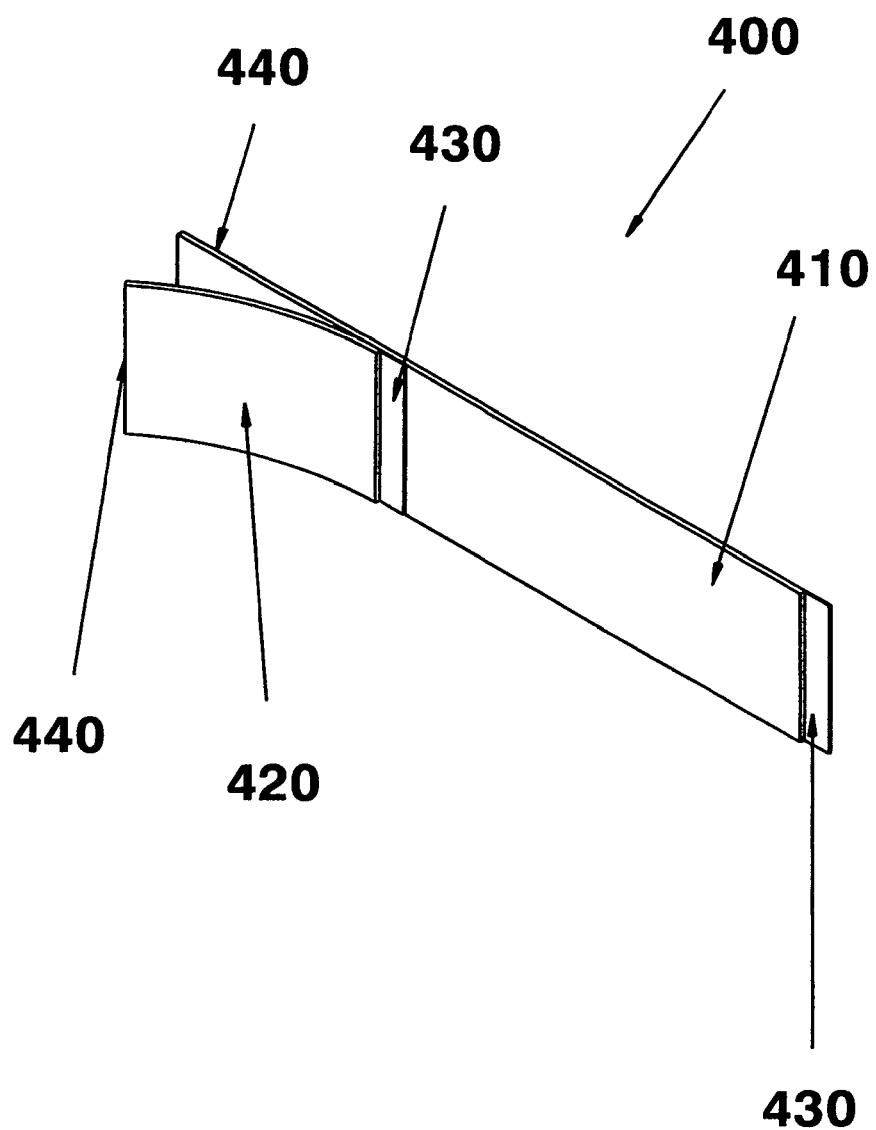
FIG. 6 is a perspective view of a fastener tab (also referred to herein as 'end tab') used with the strapping system of FIG. 4.
Figure 7:
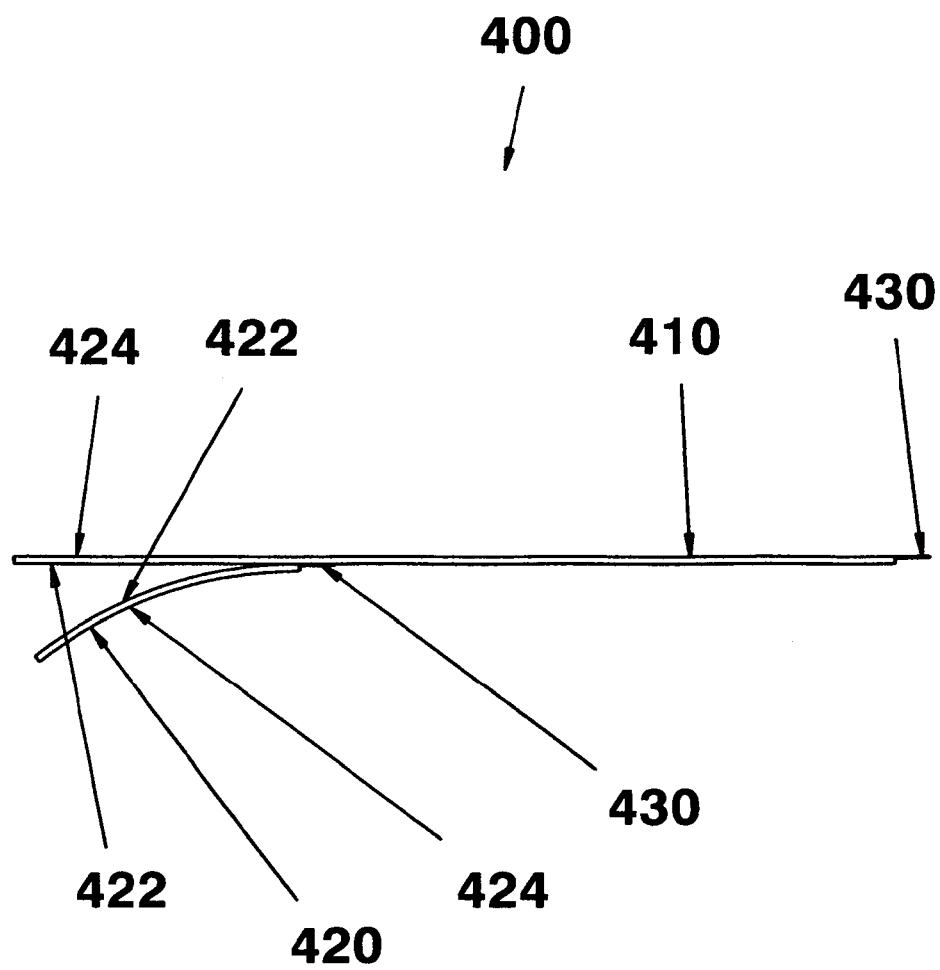
FIG. 7 is a top view of the end tab shown in FIG. 6.
Figure 8:
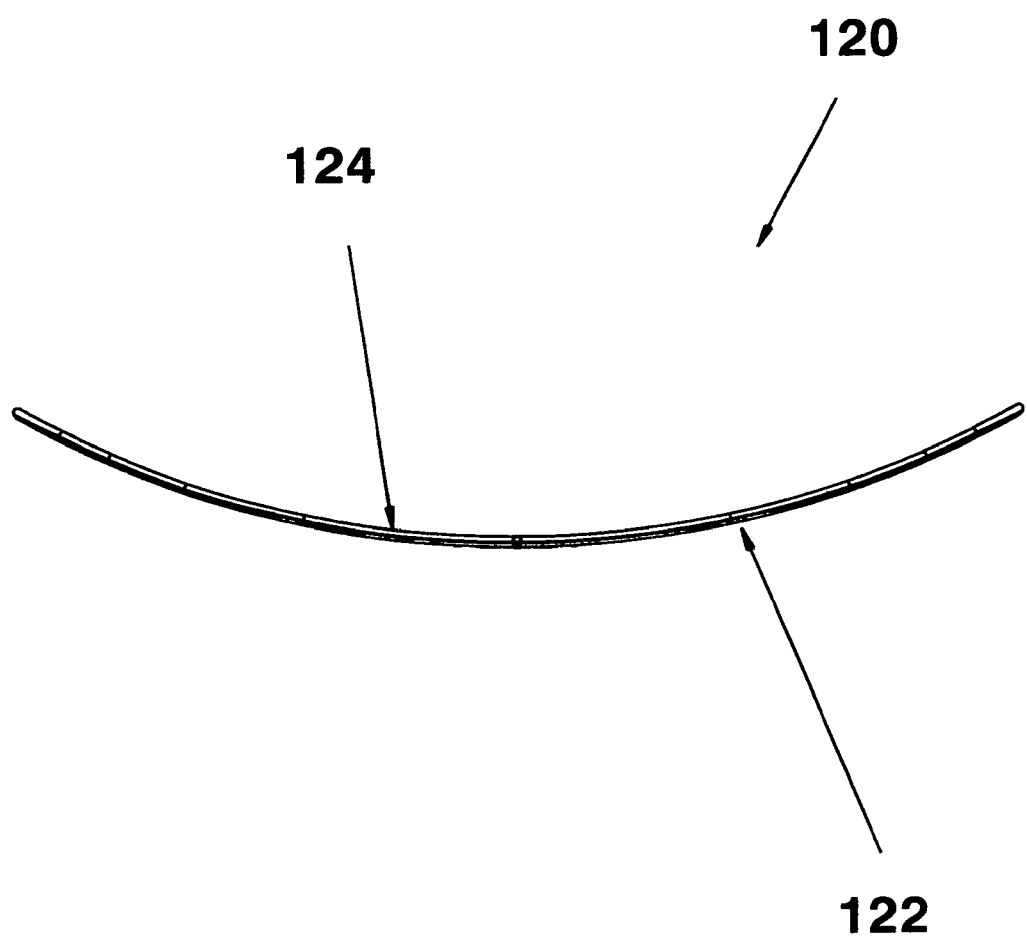
FIG. 8 is a top view of the two components forming the pouch/envelope shown in FIG. 5 that envelopes the abdominal support panel shown in FIG. 9.
Figure 9:
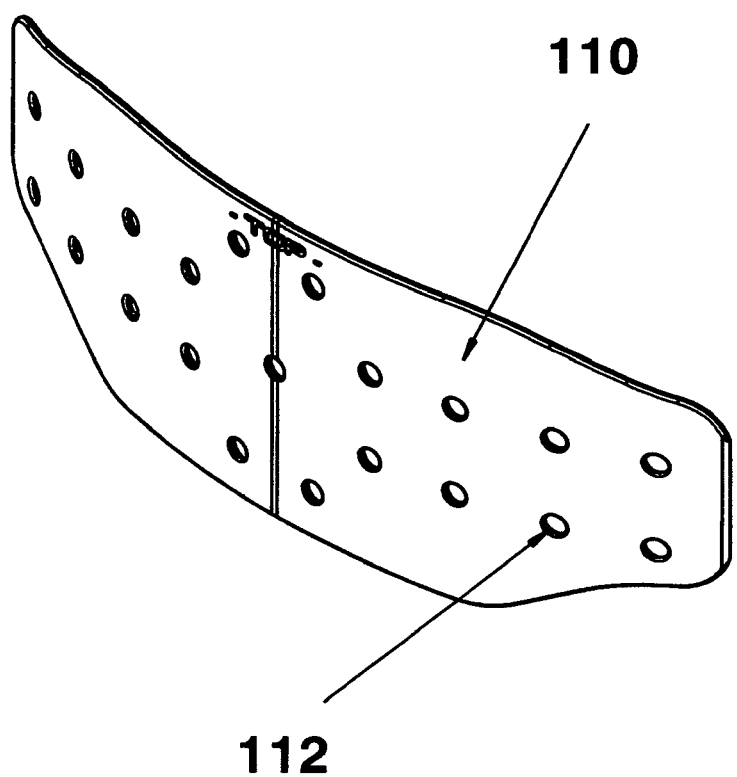
FIG. 9 is a perspective view of an abdominal support panel usable as a part of the abdominal support assembly shown in FIG. 5.
Figure 12:
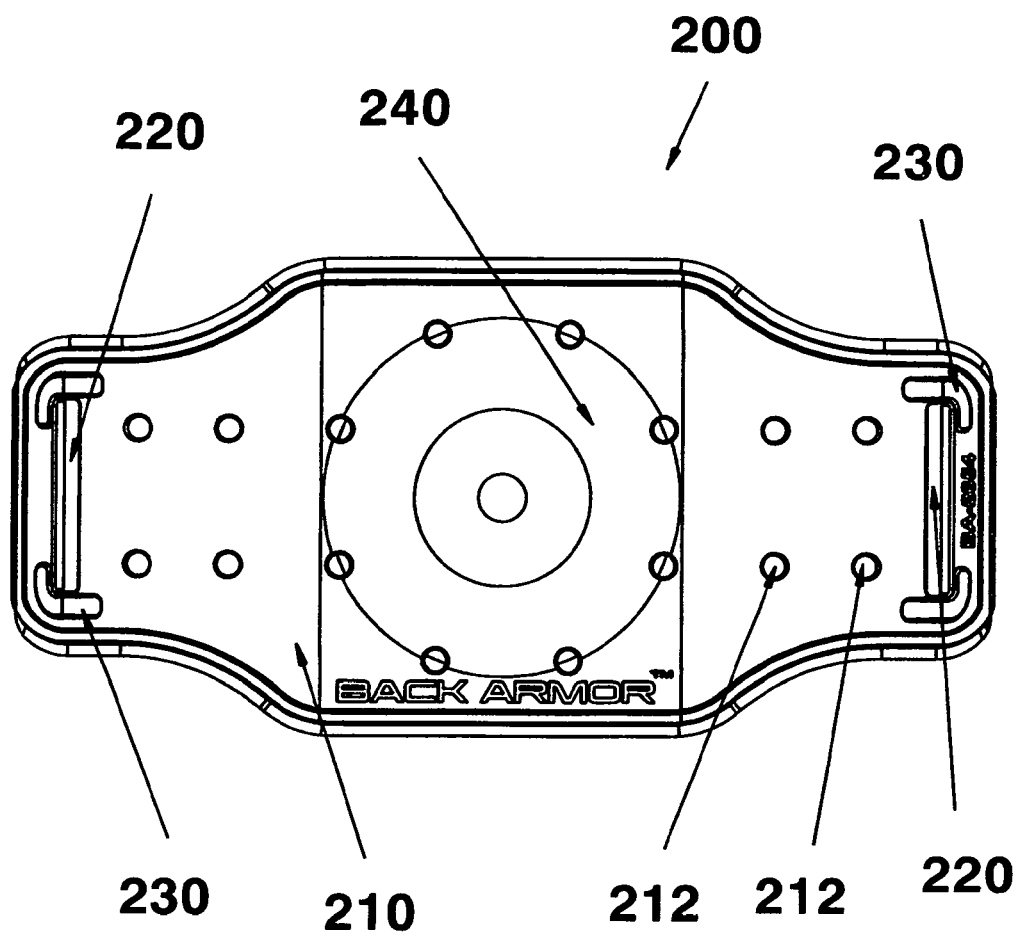
FIG. 12 is a front view the lumbar support panel used as a part of the lumbar support assembly of FIG. 10.
Figure 13:
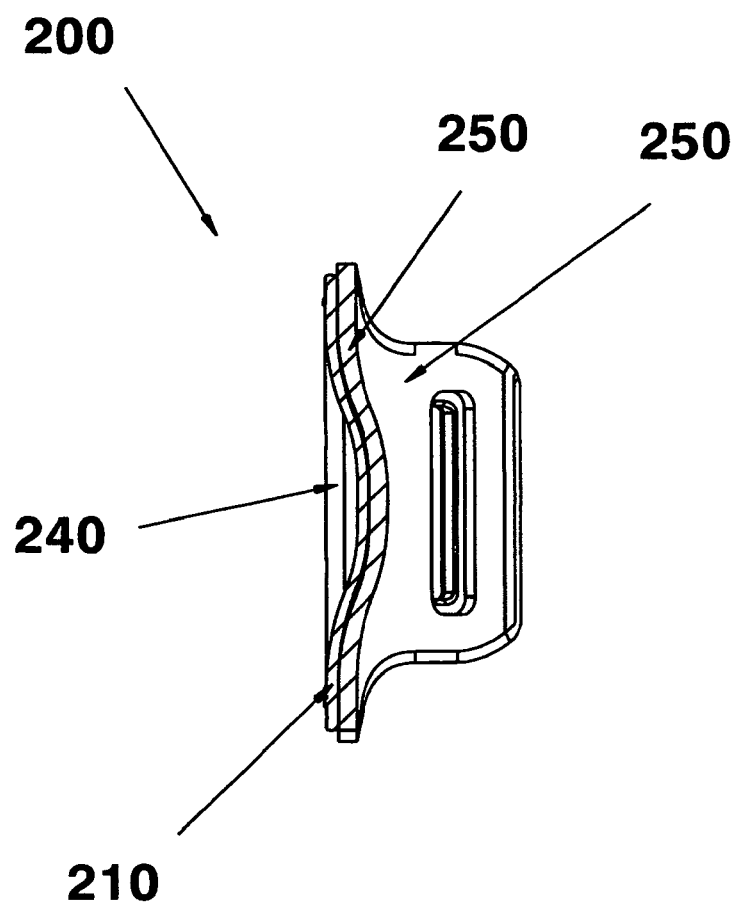
FIG. 13 is a sectional view of approximately one-half of the lumbar support panel shown in FIG. 12.
Figure 14:
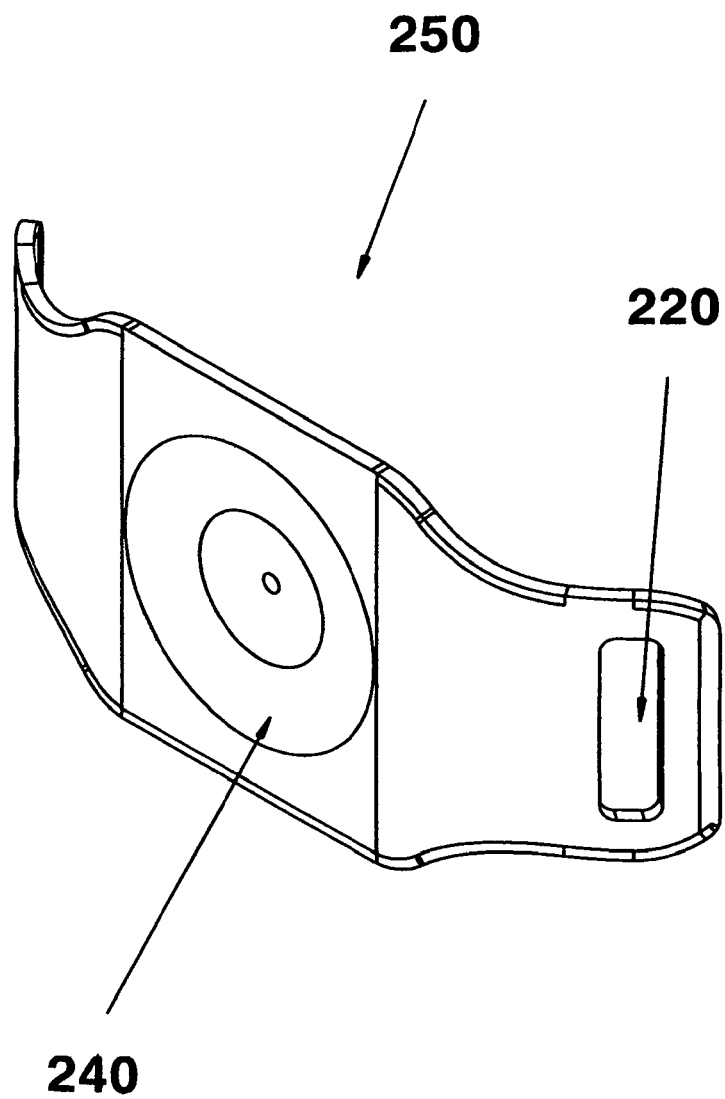
FIG. 14 is a perspective view of the foam backing used with the lumbar support panel of FIG. 10.

The lumbar region of the lower back targeted by the dome 240 of the lumbar support assembly 200 is often the most troublesome portion of the back to treat and protect, since it is difficult to support this area due to its curved shape. One advantage of the conformable back brace is that the specific dome 240 shape used as a part of the lumbar support assembly 200 may be manufactured in more than one size, and as such is able to conform to the back contours of most people wearing it. Although not limited thereto, it is commonly anticipated that each lumbar support panel 210 will be pre-molded to the shape of a human back, and it is contemplated that several sizes will be commonly available. In at least one aspect, the abdominal support panel 110, the lumbar support panel 210, or both, may be manufactured at least in part from a thermoplastic material. However, as one skilled in the art can appreciate, the abdominal support panel 110 and the lumbar support panel 210 may be manufactured from any substantially rigid material with conformable qualities. Additionally, either one may also be manufactured in a one-size-fits-most modality. FIG. 1 shows an exemplary aspect of the conformable back brace, which includes the lumbar support assembly 200, strapping system 300, and abdominal support panel 110. In contrast, FIG. 2 shows the strapping system 300 (including envelope/pouch 120) used to support abdominal support panel 110 and lumbar support panel 210 comfortably against the torso of a user in a biasing manner. Furthermore, FIG. 3 shows belt assembly 310 (without the envelope/pouch 120), and FIGS. 4 and 5 show abdominal support panel 110 in extended configurations, with FIGS. 6 and 7 showing the fastener end tab 400 in enhanced detail, which is a part of belt assembly 310, while FIG. 8 shows more detail about envelope/pouch 120 and FIG. 9 shows a front view of the abdominal support panel 110 used within envelope/pouch 120. Finally, FIGS. 10-13 show various views of lumbar support assembly 200, with FIG. 14 showing the foam backing 250 associated with interior surface of lumbar support panel 210 intended for facing the torso of a user.

Figure 10:
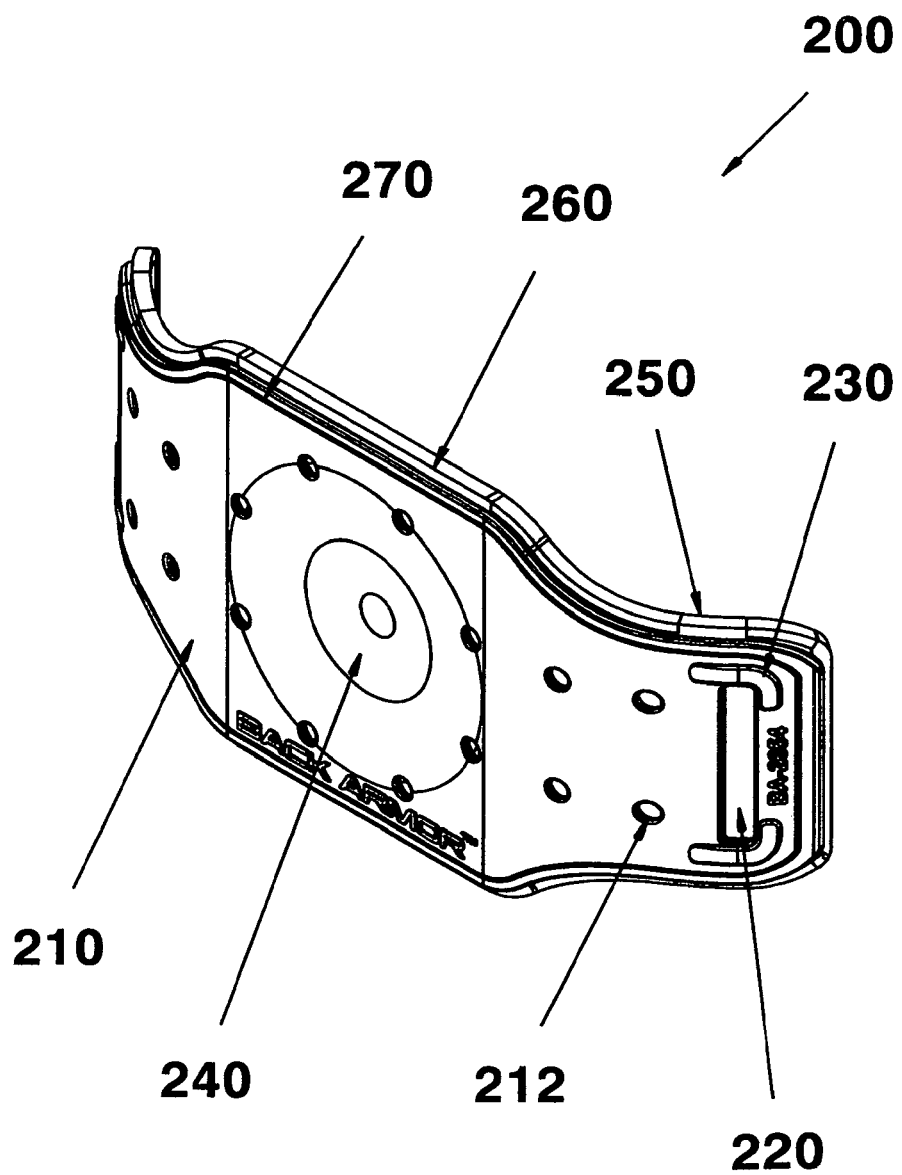
FIG. 10 is a perspective view of a lumbar support assembly.

In another aspect, as shown in FIG. 1, the lumbar support panel 210 can have a central dome 240 and one or more vertical slots 220 positioned at each end thereof, which have sufficient length and width to accommodate the insertion therethrough of a belt 320 with a Y-shaped fastening end tab 400 on one of its opposing distal ends 302. As also shown in FIG. 1, belt 320 is associated with the surface of pouch/envelope 120 facing away from a user's torso, and inserted through the slots 220 on the opposing ends of lumbar support panel 210. The foam backing 250 of FIG. 14 is also identified in FIG. 1 as being secured over the torso-facing surface of lumbar support panel 210, including its centrally located dome 240. As can be further seen in FIG. 14, the foam backing 250 can also have slots complementary to those in lumbar support panel 310, and as shown in FIGS. 10 and 12, slot reinforcement is also an option. As further shown in FIG. 1, the association of belt 320 with pouch/envelope 120 and lumbar support panel 210 places them in opposing positions with respect to one another, so that they can be firmly biased by belt 320 respectively against the opposite sides (front and back) of a user's torso (not shown). In yet another aspect, the end tab assembly 400 with selective surfaces comprising hook material associated with one distal end 302 of belt 320, the coins 340 comprising hook material that are secured to belt 320, and a strip of hook material 330 associated with envelope/pouch 120, in combination further assist in the securing of the distal ends 302 of belt 320 and maintain the bias provided thereby, while belt 320 is in its usable position biasing pouch/envelope 120 and lumbar support panel 210 in opposing positions to one another against a user's torso. Although not shown in FIG. 1, but visible in FIGS. 5 and 9, a rigid abdominal support panel 110 is placed within, and substantially fills, a defined interior volume of envelope/pouch 120. It is the envelope/pouch 120 that allows forces to be evenly distributed across abdominal support panel 110 for enhanced comfort of its user and less opportunity for premature fatigue and/or failure of abdominal support panel 110. In the alternative, although not shown, it is contemplated for the reverse to occur, and for abdominal support panel 110 to comprise vertical slots 220 and for lumbar support panel 210 to be enclosed in substantial part within an envelope/pouch 120. Belt 320 can be integral with envelope/pouch 120, permanently connected thereto (such as via adhesive or stitching, but not limited thereto), or temporarily attached to envelope/pouch 120 (such as via easily releasable fasteners, including hook-and-loop fasteners, but not limited thereto). Furthermore, in another aspect, although not limited thereto, the front member 122 of pouch/envelope 120 (contemplated for facing away from a user's torso) would comprise a durable fabric, such as but not limited to ballistic nylon. Also in this aspect, pouch/envelope 120 can comprise a back member 124 (configured for placement adjacent to a user's torso) that is made from breathable material, such as but not limited to foam. Back member 124 can be secured to the panel positioned within envelope/pouch 120, such as via adhesive or glue. In at least one aspect, the breathable material used for the back member 124 of pouch/envelope 120 would comprise BREATHOPRENE. Additionally, lumbar support panel 110 may also be substantially covered by BREATHOPRENE to keep the thermoplastic material from coming in contact with the user's skin and may further include additional comfort-enhancing padding (such as the foam backing 250 for lumbar support panel 110 shown in FIG. 14, but not limited thereto). Since the belt is adjustable to people of differing stature via belt 320, and to allow good force distribution across envelope/pouch 120 when sized for a person with a small torso circumference near the lower limit of adjustability of the conformable back brace, the attachment of belt 320 to pouch front member 122 does not extend completely across pouch front member 122. This provides small areas on both sides of envelope/pouch 120 where the opposing ends of lumbar support panel 210 are able to subduct under the ends of envelope/pouch 120 instead of having the ends of the abdominal support panel 110 pressing against the ends of lumbar support panel 210 and thus potentially causing interference with the smooth/fluid pulling of belt 320 needed to properly bias the conformable back brace against a user's torso. The smooth/fluid pulling of belt 320 used to bias the conformable back brace against a user's torso allows the very desirable advantage of infinite adjustment, in contrast to the adjustment in pre-established increments that is common to prior art back brace devices.

As mentioned above and although not shown, it is further contemplated for a pouch/envelope similar in concept to the pouch/envelope 120 shown in FIG. 1, but enlarged and reconfigured for closely fitting around lumbar support panel 210. In the aspects of the belt in which lumbar support panel 210 is enveloped by a pouch/envelope 120 in lieu of abdominal support panel 110, the abdominal support panel 110 would comprise one or more vertical slots 220 on its opposing ends (such as but not limited to the configuration of those shown in FIG. 1 on lumbar support panel 210) that are configured to allow insertion of belt 320 therethrough for its support against a user's torso, and lumbar support panel 210 (positioned within envelope/pouch 120 would require no vertical slots 220. In essence, the strapping system 300 otherwise disclosed herein could be reversed and comprise an enlarged envelope/pouch 120 configured to hold lumbar support panel 210 instead of abdominal support panel 110.

As further shown in FIGS. 1-5, and also in FIGS. 6-7, one distal end 302 of the belt 320 comprises a secure but easily-releasable end tab assembly 400, with conventional hook and loop fastening means in selected locations. Some variation from the configuration shown is contemplated in other aspect, such as but not limited to the length and width dimensions of elongated member 410, short member 420, and legs 440. In at least one aspect, the hook and loop fastener used is VELCRO. In at least one other aspect, a strip of easily-releasable fastener material 330 (see FIG. 1) is attached to the surface of belt 320 facing away from a user's torso (or otherwise in front of envelope/pouch 120) that can be used selectively and adjustably to attach/secure the distal ends 302 of belt 320 to provide the biasing needed to secure abdominal support panel 110 and lumbar support panel 210's torso. The perimeter configuration and dimension of the strip of easily-releasable fastener material 330 shown in FIG. 1 should not be considered as a limiting feature of the conformable back brace as long as it effectively fulfills its intended functions. In the alternative, such a strip of easily-releasable fastener material 330 could be attached to a portion of envelope/pouch 120. Thus, belt 320, which is permanently attached to, integral with, or detachable from, a portion of envelope/pouch 120, has distal ends 302 that are inserted through the vertical slots 220 associated with the opposing ends of the lumbar support panel 210 and folded back toward envelope/pouch 120 for releasable attachment to coins 340 and/or a strip of hook material 330 secured onto a portion of envelope/pouch 120 or belt 320, such that a user's torso becomes positioned between a combination of envelope/pouch 120 (while it contains abdominal support panel 110), lumbar support panel 210, and belt 320, with belt 320 biasing lumbar support panel 210 and the abdominal support panel 110 that is substantially encased within envelope/pouch 120 securely against the perimeter of a user's torso. The number, positioning, configuration, and dimension of the vertical slots 220 shown in FIG. 1 should not be considered as limiting as long as they are able to receive belt 320 therethrough. For a custom fit, the distal ends 302 of belt 320 may be manufactured for surrounding the torso of the largest user contemplated for using the belt, and then cut to size for a user so that the distal ends 302 of belt 320 can be comfortably secured in place against the strip of fastener material 330 without undue excess extending beyond strip 330. An end tab assembly 400 (see FIGS. 6 and 7) can be used on one distal end 302 of belt 320 for securing belt 320 and allow its biasing action for abdominal support panel 110 and lumbar support panel 210 to be maintained while all three extend around and against the torso of a user. Although FIGS. 4 and 5 only shown two coins 340 of hook material for use in engaging belt 320 during custom fitting and use of the conformable back brace, more or less than two coins 340 could be also used.

As also shown in FIGS. 6 and 7, each Y-shaped end tab assembly 400 can have an elongated member 410 and a short member 420, that are secured together via a heat weld 430 to create two opposing legs 440. In addition, and/or in the alternative, elongated member 410 and short member 420 may be sewn or glued together to form legs 440. In one aspect, the interior surfaces 422 of legs 440 would comprise hook material or other easily-releasable fastening material complementary to the material from which belt 320 is made. However, it is contemplated for the exterior surfaces 424 of each opposing leg 440 to contain material not matingly complementary to the strip of easily-releasable fastener material 330 material associated with envelope/pouch 120. It is also contemplated for the exterior surfaces 424 of each opposing leg 440 to not be matingly complementary to clothing fabric placed over it. Elongated member 410 and short member 420 may each be substantially planar in configuration, and each leg 440 may have a length dimension similar to that of the other leg 440, although not limited thereto. Furthermore, the side of the portion of elongated member 410 not forming a leg 440 (and which is intended to face a user's torso would comprise a releasable fastener means matingly complementary to the second distal end 302 of belt 320 that is not secured between legs 440, and the reverse side of the portion of elongated member 410 not forming a leg 440 (and which is intended to face away from a user's torso would be configured to avoid/resist attachment to clothing fabric placed over it. In addition, two heat welds 430 are optionally associated with elongated member 410. The first is used to secure short member 420 to elongated member 410 to form legs 440 (although as is mentioned above, stitching, adhesive, and/or other attachment means may be alternatively used in place of the first heat weld 430 for such connective purpose). The second heat weld 430 is positioned at the end of the elongated member 410 opposed from legs 440, and since the portion of elongated member 410 where the second heat weld 430 is present is void of hook structure and does not stick to the opposing distal end 302 of belt 320 positioned immediately below it when belt 320 becomes secured around a user's torso, the second heat weld 430 creates a small detached flap that is easily lifted and grasped by a user's fingers to begin the process of peeling end tab assembly 400 away from the opposing distal end 302 of belt 320 positioned immediately below it for rapid release of belt 320 biasing and prompt removal of the conformable back brace from around the user's torso.

FIGS. 8 and 9 respectively show the envelope/pouch 120 of strapping system 300 and the abdominal support panel 110 of the abdominal support panel 110. FIG. 8 shows the front member 122 of envelope/pouch 120 secured to the back member 124 of envelope/pouch 120. Envelope/pouch 120 is shown with a very slim profile that allows abdominal support panel 110 to substantially fill the defined interior volume between front member 122 and back member 124. The thin profile of envelope/pouch 120 allows for a better cosmetic effect under clothing that covers it. In FIG. 9, the one aspect of the support panel 110 is shown with a plurality of holes 112 there through that decrease the weight of abdominal support panel 110 to help make abdominal support assembly panel 110 more lightweight for user comfort, with holes 112 also making abdominal support panel 110 more breathable. However, the size, perimeter configuration, number, and positioning of holes 112 may differ from that shown in FIG. 9. Also, as shown in FIG. 8 but not identified by numerical marking, the top edge of abdominal support panel 110 may be marked with the word "TOP", an upwardly-directed arrow (not shown), or other designation indicating the intended orientation of abdominal support panel 110 when employed against a user's torso. Furthermore, while the surface texture of abdominal support panel 110 appears smooth in FIG. 9 and void of decorative markings, the lack of raised texture and design feature should not be considered as limiting.

When looking at the lumbar support assembly 200 in FIGS. 10-13, and its foam backing 250 in FIG. 14, the overall shape of lumbar support assembly 200 can be seen to be complementary to the cross-sectional shape of a human back. As shown best in FIGS. 11 and 13, the central portion of lumbar support panel comprises a centrally-positioned and convex dome 240 that protrudes into the back lumbar area of the lower lumbar region of a user's torso (not shown), to thereby define an ideal contour that allows lumbar support panel 210 for optimal support of both the user's spine and muscles associated with the spine. Thus, during use of lumbar support panel 210, the back muscles will seek the ideal back profile best suited for the human body and the muscles associated with the spine will be toned and conditioned to replicate the ideal profile provided by dome 240, and thereby alleviate muscle strain in the user's lower back. Concurrently with the toning of a user's spine and back muscles, the user's abdominal muscles will also become realigned and toned. FIG. 10 shows lumbar support panel 210 having multiple holes 212 there through and ribbed slot reinforcement 230 both above and below the one visible vertical slot 220. Although slot reinforcement 230 both above and below vertical slots 220 is contemplated, both are not required in all applications, and the size, placement, and configuration of slot reinforcement 230 can be different from that shown. Furthermore, the size, perimeter configuration, number, and positioning of holes 212 shown in FIGS. 10 and 12 are only representative and holes 212 may be different therefrom as long as they fulfill their ventilation and weight reducing objectives. Also in FIG. 10, the foam backing 250 (see also FIG. 14) can be slightly oversized relative to lumbar support panel 210 and secured against the back of lumbar support panel 210 by adhesive 260 and/or stitching 270, which are exemplary means of attachment. In the alternative, foam backing 250 can slightly oversized relative to lumbar support panel 210, and then merely positioned between lumbar support panel 210 and the torso of a user as belt 320 is tightened.

Figure 11:
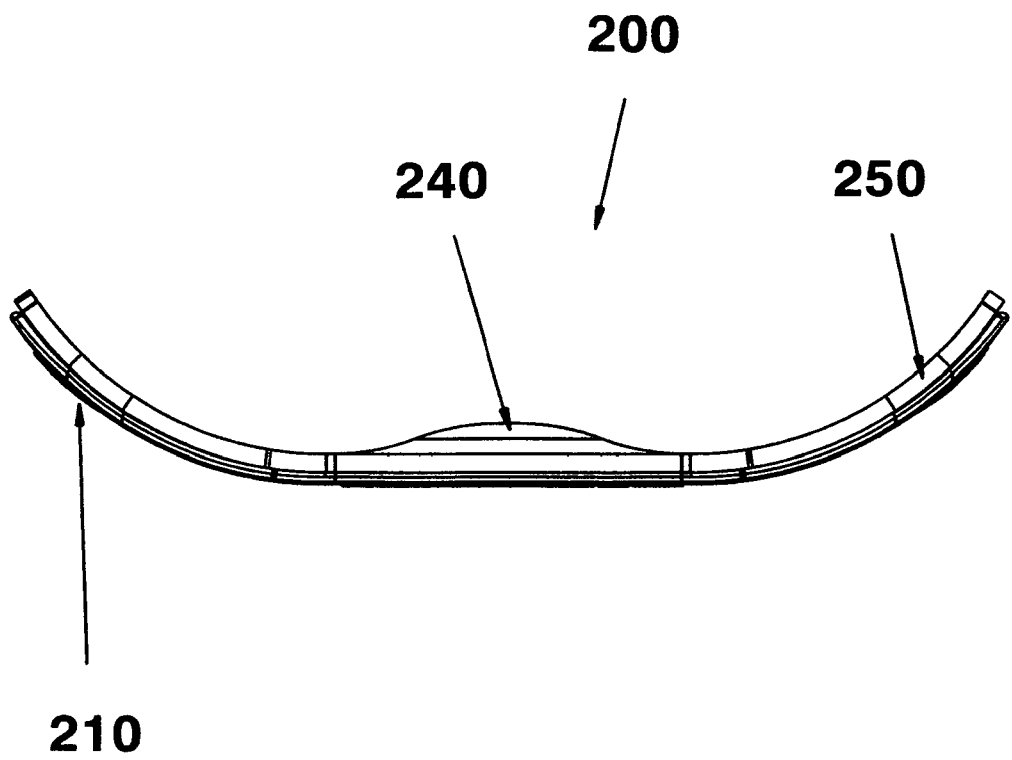
FIG. 11 is a top view the lumbar support assembly shown in FIG. 10, including the lumbar support panel in FIG. 12 and the foam backing shown in FIG. 14.

Although such markings are not identified by numerical designation in FIG. 10, lumbar support panel 210 is shown with alpha-numeric markings (which can include associated logos, model numbers, manufacturer identifications, and/or other information relevant to the source and/or use of the conformable back brace). Furthermore, while the surface texture of lumbar support panel 210 appears smooth and void of design, the lack of texture and design shown should not be considered as limiting. The foam backing 250 in FIG. 14 is also shown in FIGS. 11 and 13 in a position to cushion dome 240 when lumbar support panel 210 is biased by belt 320 against the torso of a user. Foam backing 250 may comprise anti-microbial features and be secured to the lumbar support panel 210 (or a similar backing secured to abdominal support panel 110) via adhesive and/or stitching. Furthermore, any backing used for abdominal support panel 110 (and even abdominal support panel 110 itself) can be glued or otherwise secured to back pouch panel 124. In the reverse, when lumbar support panel 210 is positioned within envelope/pouch 120, its backing 250 can be glued or otherwise secured to back pouch panel 124.

In at least one aspect, the depth of dome 240 may be approximately ¼ inch and it may comprise a 3½-inch diameter dome or hemisphere allowing it to nestle in the lower lumbar area of a user's back. In addition, although not shown in the accompanying illustrations, belt 320 may include some elasticity in the material from which it is made, or in the form of one or more stretchable portions which provide a safety precaution for its user by giving some stretch to belt 320. Belt 320 may be cut to size to provide a custom fit for user's of differing stature, as well. In spite of the tremendous support provided to both the front and back of a user's body by the conformable back brace device, it is comfortable and can be worn easily during sporting activity such as golf or tennis for the benefit of the person wearing it, or during periods of inactivity. In summary, the conformable back brace device provides a pre-formed lumbar support panel 210 and pre-formed abdominal support panel 110 can be firmly affixed to the wearer. In addition, the perfect back configuration provided by the conformable back brace benefits users by realigning back muscles and the back spinal column, while concurrently toning muscles in the back and around the spinal column To use the conformable back brace device, a user would first have to install one of the panels (lumbar support panel 210 or abdominal support panel 110, as indicated by the panel's shape and lack of vertical slots 220) into any envelope/pouch 120 having an opening for such use. However, in one aspect, the abdominal support panel 110 is already permanently inserted into envelope/pouch 120 during manufacture and there is no fastener (such as VELCRO or a zipper) to open and close so as to allow the conformable back brace's user to insert and remove support panels (110 or 210) from envelope/pouch 120. The lack of fasteners in one aspect will ensure that the partially asymmetrical abdominal support panel 110 remains in the upright position needed for use. However, when envelope/pouch 120 is configured to fit closely around abdominal support panel 110, the opportunity for incorrect orientation of abdominal support panel 110 is greatly reduced. Inversion of lumbar support panel 210 is not an issue, as its shape allows it to work equally well in an upright or upside down orientation. As a result, a conformable back brace user is generally presented with two sub-assemblies to manipulate for custom-fitting and use, the lumbar support panel (with backing 250) and the strapping system 300 with its associated envelope/pouch 120 already holding abdominal support panel 110. Prior to moving the abdominal support panel 110, lumbar support panel 210, and strapping system 300 close to a user's torso (not shown), the user would place one of the distal ends 302 of the strapping system's belt 320 through a vertical slot 220 on one end of lumbar support panel 210. Subsequently, and with all of the components of the conformable back brace close to the torso, the user would then insert the other distal end 302 of belt 320 through a vertical slot 220 on the other end of lumbar support panel 210. After positioning envelope/pouch 120 over the abdomen and lumbar support panel 210 across the lower back, all that remains for the user to do is to grasp each distal end 302 of belt 320 in the strapping system 300 with a different hand and pull both distal ends 302 forwardly toward envelope/pouch 120. Coins 340 of hook material can be used to temporarily secure belt 320 while initial length adjustment of each of the opposing ends 302 of belt 320 has occurred by trimming excess belt 320 material therefrom and attaching a specifically configured end tab 400 to one of the belt's distal ends 302 so that the end tab 400 and the opposing distal end 302 of belt 320 each extend over a substantial portion of the strip of hook material 330 extending horizontally in front of the envelope/pouch 120. Thereafter, securing the two support panels (110 and 210) into their optimal positions of use is easily accomplished by a simple and quick fastening of the opposing distal ends 302 of belt 320 to the strip of hook material 330 extending in front of envelope/pouch 120. Tension derived from tightening and securing belt 320 is spread evenly across envelope/pouch 120, evenly dispersing the force present across abdominal support panel 110 (or in reverse across the lumbar support panel 210 should it be placed into envelope/pouch 120 instead). In prior art devices, force is applied to the ends of its abdominal support structure via slots, which in addition to causing user discomfort, also places such abdominal support panels structure at risk for cracking and breaking. Another benefit of enclosing a support panel (110 or 210) within an envelope/pouch 120, wherein straps are attached to the envelope/pouch 120 instead of the support panel (110 or 210), is that the thickness dimension of the support panel (110 or 210) within envelope/pouch 120 can be reduced over that needed in prior art devices to provide better concealment under clothing. The end tab 400 can be used to securely fasten the distal ends 302 of the strapping system belt 320 and can generally have a Y-shape with selected surfaces having hook material, and other surfaces without hooked material, so as to prevent inadvertent engagement with any user clothing positioned over it. Release of the belt from around the torso of its user is also fast and easy, with both distal ends 302 of belt 320 being easily released from the front strip of hook material 330 extending in front of envelope/pouch 120. The user can then withdraw one of the distal ends 302 of belt 320 from its adjacent vertical slot 22 in the lumbar support panel 210 to provide an opening to employ in removing the conformable back brace from the user's torso. Movements made by the user in attaching and releasing the conformable back brace from around his or her torso, including the pulling forward of both distal ends 302 of belt 320 toward envelope/pouch 120, are movements that one with back pain can easily accomplish with minimal discomfort. Prior art back brace devices commonly allow for user adjustment in pre-determined increments. However, the strapping system 300 allows for infinite adjustment between its largest and smallest circumference dimensions. Use of end tab 400 allows for expedited custom fitting without any sewing, bonding, or welding. A custom fit that properly sizes the belt 320 of strapping system 300 prevents any excess belt 320 material from extending beyond envelope/pouch 120, making it easier to conceal the conformable back brace under clothing. Furthermore, if the attachment of belt 320 to pouch front member 122 does not extend completely across pouch front member 122, small areas on both sides of envelope/pouch 120 are provided where the opposing ends of lumbar support panel 210 are able to subduct under the ends of envelope/pouch 120 (instead of having the ends of the abdominal support panel 110 pressing against the ends of lumbar support panel 210 where they would have the potential for causing interference with the smooth/fluid pulling of belt 320 needed to properly bias the present invention against a user's torso). The smooth/fluid pulling of belt 320 used to bias the conformable back brace against a user's torso allows the very desirable advantage of infinite adjustment, in contrast to the adjustment in pre-established increments that is common to prior art back brace devices.

Although many embodiments of the present invention have been disclosed herein, it is to be understood by those skilled in the art that many other modifications and embodiments of the present invention will come to mind to which the invention pertains, having the benefit of the teaching presented in the foregoing description and associated drawings. It is thus to be understood that the invention is not limited to the specific embodiments disclosed hereinabove, which have been provided only as examples, and that many modifications and other embodiments are intended to be included within the scope of the appended claims. Moreover, although specific terms are employed herein, as well as in the claims which that follow, such terms should be construed only in a generic and descriptive sense, and have not been provided for the purpose of limiting the disclosed invention, nor the claims which follow.

INDUSTRIAL APPLICABILITY

Presented herein is a multi-component brace assembly primarily intended for providing immobilization of the human back, and more particularly to a conformable back brace employed for providing simultaneous abdominal and lumbar support to its user, which when worn produces intracavitary pressure which may reduce load on intravertabral discs. Both preventative and treatment applications are contemplated. Applications may also include, but are not limited to, medical device applications, occupational safety applications, and sports applications, as well as body armor and protective gear applications. In addition, it has a lightweight construction, can easily and promptly be custom-fit to a user without employing special fabrication techniques, such as, but not limited to, welding, gluing, sewing, and the like, which would require additional equipment or tools by the user and/or fitter. It is quickly and easily placed into its usable position around the torso by its user once custom-fit, and it has a slim profile that allows easy concealment under clothing according to user preference and/or need, which is not always possible with prior art devices. In one configuration, it includes an abdominal support panel substantially enclosed within a support envelope that distributes the tension provided by a belt associated with the envelope across the abdominal support panel, thereby reducing focused tension on any specific portion of the abdominal support panel that may otherwise increase the potential for its breakage. Having the rigid abdominal support panel enclosed in an envelope also provides enhanced comfort for the user. A lumbar support panel having a dome-shaped protrusion that complements the lumbar contour of the user's back, and assures proper placement of the lumbar support panel against the user's back. The belt associated with the envelope is employed to quickly and easily place the abdominal support panel and the lumbar support panel in an opposed biasing arrangement respectively against the abdomen and lower back of a user, and also allows infinitely adjustably selection of the biasing force to accommodate the needs of its user. Spinal and lower back muscle pain are chronic problems for many people. Day-to-day activity requiring movement of the back can lead to further muscular aggravation, only to reach the point in some individuals where all but the most potent pain relief medication, or surgery, is needed to have any effect. In order to help alleviate lower back pain, prevent future injury, and/or aid in recovery, a wide variety of muscular strain reducing devices for the lower back have been tried, ranging from elastic wrap-type supports to individual solid support fixtures placed longitudinally along the back to restrain its movement. However, many of these longitudinally-extending devices have the disadvantages of being very heavy, too hot to wear, are not infinitely adjustable, require special tools or techniques for proper fitting (i.e. welding, gluing, sewing, bending, and the like), can be burdensome by unduly restricting movement, and/or do not provide the proper support and alignment to be useful. In contrast, the present invention is able to provide simultaneous lumbar and abdominal support and alignment, produces intracavitary pressure which may reduce load on the intravertabral discs, utilizes an integrated strapping system that allows the user and/or fitter to quickly and easily customize the support for the user, without the need for special tools or fabrication equipment/techniques, while being lightweight and comfortable. Furthermore, it can be worn not only while sedentary, but also during strenuous physical activity, such as but not limited to golf, tennis or other sports, in the work place while one sits for long periods, and when any physical work is required.

What is claimed is:

1. A conformable back brace, comprising:
   two substantially rigid support panels comprising:
      an abdominal support panel having opposed distal portions and configured to at least generally conform to at least a portion of a user's abdomen region; and
      a lumbar support panel configured to at least generally conform to at least a portion of the user's lumbar region, the lumbar support panel having opposed distal portions and a dome protruding centrally therefrom; and
   a strapping system having an envelope defining an interior volume configured to envelop at least a portion of the abdominal support member, the envelope also having opposing distal portions, and the strapping system also comprising a belt attached to an exterior portion of the envelope, the belt further configured for secure biasing of the abdominal support panel and the lumbar support panel respectively against the abdominal and lumbar regions of a user;
   wherein at least one slot is defined in each of the opposed distal portions of the lumbar support panel, the slots also configured and dimensioned for insertion of the belt therethrough, so that when the strapping system is used to bias the lumbar support panel longitudinally across a user's lower back, the dome becomes positioned against the user's lumbar region.

2. The conformable back brace of claim 1, further providing at least one two-part fastener associated with the envelope, wherein the belt has two opposing distal ends each configured to pass through a different one of the slots on the lumbar support panel, and further wherein the belt is also configured for secure attachment of at least one of the opposing distal ends to the at least one two-part fastener associated with the envelope to provide the biasing forces needed for positioning the dome of the lumbar support panel against a user's lumbar region.

3. The conformable back brace of claim 2, wherein the two opposing distal ends of the belt are each configured to function as one part of a two-part releasable fastener and the envelope is configured for selective complementary engagement with the opposing distal ends of the belt and selectively adjustably, non-incremental attachment between the opposing distal ends of the belt with the envelope.

4. The conformable back brace of claim 3, wherein the opposing distal ends of the belt with the envelope are configured to function together as a hook and loop fastener.

5. The conformable back brace of claim 1, further comprising an end tab configured for attachment to one of the opposing distal ends of the belt and temporary association with the envelope for the one of the opposing distal ends of the belt to which the end tab is attached, wherein the end tab comprises:
   an elongated member having two opposed flat surfaces, hook material on one of the opposed flat surfaces; and
   a short member having two opposed flat surfaces and hook material on one of the opposed flat surfaces, the short member secured to the elongated member in a manner that creates two legs each having an interior face comprising hook material, wherein the hook material on the interior surfaces of the legs in combination provides secure attachment of the legs to one of the distal ends of the belt.

6. The conformable back brace of claim 1, wherein the belt is integral with the envelope.

7. The conformable back brace of claim 1, wherein the protruding dome is substantially convex.

8. An end tab configured to attach to one of the distal ends of the belt in claim 1, the end tab comprising:
   an elongated member comprising a first releasable fastener surface configured for releasable attachment to a second releasable fastener surface of the envelope, wherein the first releasable fastener surface is configured to matingly and releasably attach to the second releasable fastening surface and wherein the first releasable fastening surface is not configured to mate with or attach to itself and the second releasable fastening surface is not configured to mate with or attach to itself; and
   a short member secured to the elongated member in a manner that creates two leg portions each having an interior face comprising the first releasable fastener surface configured for attachment to one of the distal ends of the belt, wherein the distal ends of the belt comprise the second releasable fastener, and wherein, when the end tab is attached to one of the distal ends of the belt, the end tab is configured to attach the distal end of the belt to the envelope via the end tab.

9. The end tab of claim 8, wherein the elongated member comprises a surface without fastening capability that is positioned to face remotely from the panels so that contact of the surface without fastening capability with clothing placed over the elongated member avoids attachment with the elongated member.

10. The end tab of claim 8, wherein the first releasable fastener surface comprises hook material and the second releasable fastener surface comprises loop material.

11. The end tab of claim 8, wherein the first releasable fastener surface comprises loop material and the second releasable fastener surface comprises hook material.

12. The conformable back brace of claim 1, wherein the association of the belt with the envelope does not include all of the opposed distal ends of the envelop so as to allow the opposed distal ends of the envelope to subduct under the lumbar support panel when the belt biases the lumbar support panel and the abdominal support panel close to one another with a tendency for overlap.

13. A conformable back brace, comprising:
   an abdominal support panel configured to at least generally conform to at least a portion of a user's abdomen region and a lumbar support panel configured to at least generally conform to at least a portion of the user's lumbar region and having a lumbar support element protruding therefrom, each of the support panels having opposed distal portions; and
   a strapping system having an envelope defining an interior volume configured to substantially envelop the abdominal support panel, wherein the envelope comprises opposing distal portions and the strapping system also comprises a belt attached to an exterior portion of the opposing distal portions of the envelope.

14. The conformable back brace of claim 13, wherein the opposed distal portions of the lumbar support panel each define at least one slot configured to enable the belt to pass therethrough.

15. The conformable back brace of claim 14, wherein each the belt has a distal end and wherein each the distal end is configured to pass through one of the slots on the lumbar support panel and attach thereto the lumbar support panel to bias the lumbar support panel and the lumbar support panel against a user.

16. The conformable back brace of claim 15, wherein the belt of the strapping system is integral with the envelope.

17. The conformable back brace of claim 15, wherein the envelope comprises an external face, and further wherein one the external face and the distal ends of the belt are configured to function as a two-part releasable fastener, wherein selective fastening of the distal ends of the belt to the external face selectively attach the distal ends of the belt with infinite adjustment to the external face of the envelope.

18. The conformable back brace of claim 17, wherein the opposing distal ends of the belt with the external face of the envelope are configured to function together as a hook and loop fastener.

19. The conformable back brace of claim 17, further comprising an end tab configured to attach to a portion of one of the distal ends of the belt, wherein the end tab comprises:

an elongated member comprising hook material; and a short member comprising hook material, the short member secured to the elongated member to create two leg portions each having an interior face with hook material, and further wherein hook material on the interior face of each the leg is configured for secure attachment to one of the distal ends of the belt.

20. The conformable back brace of claim 19, wherein the elongated member of the end tab further comprises a heat weld that creates a void area having no hook capability that can be used as a flap for easy finger engagement and prompt removal of the end tab from its fixed association with the envelope during use.

21. The conformable back brace of claim 13, wherein the protruding support element comprises a substantially convex dome.

* * * * *